United States Patent
Fattman et al.

(10) Patent No.: US 11,071,640 B2
(45) Date of Patent: Jul. 27, 2021

(54) ONE PIECE OSTOMY POUCH ENHANCEMENTS

(71) Applicant: ConvaTec Technologies Inc., Las Vegas, NV (US)

(72) Inventors: George Fattman, Bridgewater, NJ (US); Kimberly Murray, Bridgewater, NJ (US); Marc Lesko, Bridgewater, NJ (US); Thomas Harrit, Bridgewater, NJ (US); Nicolani Sorensen, Bridgewater, NJ (US)

(73) Assignee: Convatec Technologies Inc., Las Vegas, NV (US)

(*) Notice: Subject to any disclaimer, the term of this patent is extended or adjusted under 35 U.S.C. 154(b) by 1276 days.

(21) Appl. No.: 14/646,003

(22) PCT Filed: Nov. 20, 2013

(86) PCT No.: PCT/US2013/071098
§ 371 (c)(1),
(2) Date: Oct. 7, 2015

(87) PCT Pub. No.: WO2014/081889
PCT Pub. Date: May 30, 2014

(65) Prior Publication Data
US 2015/0320585 A1      Nov. 12, 2015

Related U.S. Application Data

(60) Provisional application No. 61/728,581, filed on Nov. 20, 2012.

(51) Int. Cl.
*A61F 5/445* (2006.01)
*A61F 5/44* (2006.01)
(Continued)

(52) U.S. Cl.
CPC .............. *A61F 5/445* (2013.01); *A61F 5/443* (2013.01); *A61F 5/4404* (2013.01);
(Continued)

(58) Field of Classification Search
CPC combination set(s) only.
See application file for complete search history.

(56) References Cited

U.S. PATENT DOCUMENTS 3,570,490 A  *  3/1971  Berger ................... A61F 5/445
                                                         604/332
4,211,224 A     7/1980  Kubach et al.
(Continued)

FOREIGN PATENT DOCUMENTS

CN      1761435 A     4/2006
CN    201160933 Y    12/2008
(Continued)

OTHER PUBLICATIONS

Australia Patent Application No. 2013347992 Examination Report No. 1 dated Aug. 31, 2017.
(Continued)

*Primary Examiner* — Tatyana Zalukaeva
*Assistant Examiner* — Guy K Townsend
(74) *Attorney, Agent, or Firm* — Taft Stettinius & Hollister LLP

(57) ABSTRACT

Provided herein are controlled evacuation devices, ostomy devices, methods for the manufacture of such devices and the use of such devices.

14 Claims, 14 Drawing Sheets

Figure 1A:
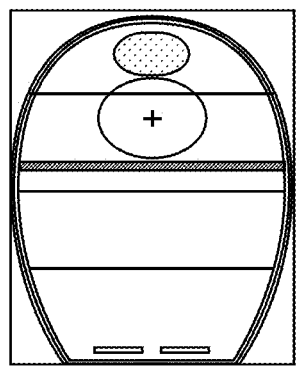

(51) Int. Cl.
*A61F 5/448* (2006.01)
*A61F 5/443* (2006.01)
*A61F 5/441* (2006.01)

(52) U.S. Cl.
CPC ............ *A61F 5/4407* (2013.01); *A61F 5/448* (2013.01); *A61F 5/441* (2013.01); *A61F 2005/4483* (2013.01)

(56) References Cited

U.S. PATENT DOCUMENTS

| | | | |
|---|---|---|---|
| 4,327,727 A | 5/1982 | Prahl et al. | |
| 4,367,732 A | 1/1983 | Poulsen et al. | |
| 4,490,145 A * | 12/1984 | Campbell | A61F 5/441 604/333 |
| 4,534,768 A | 8/1985 | Osburn et al. | |
| 4,701,169 A | 10/1987 | Steer | |
| 4,750,482 A * | 6/1988 | Sieverding | A61L 15/58 604/317 |
| 4,826,495 A * | 5/1989 | Petersen | A61F 5/441 604/333 |
| 4,917,692 A | 4/1990 | Steer et al. | |
| 5,074,852 A * | 12/1991 | Castellana | A61F 5/443 604/336 |
| 5,545,154 A | 8/1996 | Oberholtzer | |
| 5,912,059 A * | 6/1999 | Jones | A61F 5/443 428/35.2 |
| 5,961,502 A * | 10/1999 | Amery | A61F 5/443 604/332 |
| 5,976,118 A | 11/1999 | Steer | |
| 6,106,507 A | 8/2000 | Botten et al. | |
| 6,165,159 A | 12/2000 | Blanton | |
| 6,332,879 B1 * | 12/2001 | Nielsen | A61F 5/448 604/344 |
| 6,709,421 B1 * | 3/2004 | Falconer | A61F 5/441 604/335 |
| 6,723,079 B2 | 4/2004 | Cline | |
| 6,746,765 B1 | 6/2004 | Fattman | |
| 6,764,474 B2 | 7/2004 | Nielsen et al. | |
| 6,840,924 B2 * | 1/2005 | Buglino | A61F 5/443 604/337 |
| 7,090,664 B2 | 8/2006 | Holter | |
| 7,160,275 B2 | 1/2007 | Falconer | |
| 7,214,217 B2 | 5/2007 | Pedersen et al. | |
| 7,259,190 B2 | 8/2007 | Lykke | |
| 7,347,844 B2 | 3/2008 | Cline et al. | |
| 7,722,586 B2 * | 5/2010 | Mullejans | A61F 5/441 604/332 |
| 7,819,850 B2 * | 10/2010 | Mullejans | A61F 5/441 604/344 |
| 7,846,144 B2 * | 12/2010 | Ciok | A61F 5/448 604/332 |
| 8,013,206 B2 * | 9/2011 | Mullejeans | A61B 5/107 602/41 |
| 8,092,437 B2 | 1/2012 | Cline | |
| 8,096,980 B2 | 1/2012 | Cline | |
| 8,217,221 B2 | 7/2012 | Davies et al. | |
| 8,704,033 B2 * | 4/2014 | Mullejans | A61B 5/107 602/41 |
| 8,708,987 B2 * | 4/2014 | Cramer | A61F 5/443 604/344 |
| 9,233,019 B2 * | 1/2016 | Lykke | A61F 5/4404 |
| 9,452,079 B2 * | 9/2016 | Lykke | A61F 5/4404 |
| 9,549,840 B2 * | 1/2017 | Buus | A61F 5/443 |
| 2003/0004477 A1 | 1/2003 | Nielsen et al. | |
| 2004/0065232 A1 | 4/2004 | Lykke | |
| 2004/0193122 A1 | 9/2004 | Cline et al. | |
| 2005/0015065 A1 | 1/2005 | Falconer | |
| 2005/0054997 A1 | 3/2005 | Buglino | |
| 2005/0065486 A1 | 3/2005 | Fattman | |
| 2005/0075616 A1 | 4/2005 | Holter | |
| 2005/0177119 A1 * | 8/2005 | Tsai | A61F 5/445 604/332 |
| 2005/0282977 A1 | 12/2005 | Stempel et al. | |
| 2006/0184145 A1 * | 8/2006 | Ciok | A61F 5/443 604/338 |
| 2006/0200101 A1 * | 9/2006 | Mullejans | A61F 5/441 604/339 |
| 2007/0005032 A1 * | 1/2007 | Shan | A61F 5/448 604/342 |
| 2007/0027434 A1 | 2/2007 | Pedersen et al. | |
| 2007/0078418 A1 * | 4/2007 | May | A61F 5/443 604/336 |
| 2007/0123832 A1 | 5/2007 | Cline et al. | |
| 2007/0185464 A1 | 8/2007 | Fattman et al. | |
| 2008/0004580 A1 * | 1/2008 | Mullejans | A61F 5/441 604/344 |
| 2008/0269700 A1 * | 10/2008 | O'Toole | A61F 5/4405 604/332 |
| 2008/0300556 A1 * | 12/2008 | Fenton | A61F 5/4404 604/339 |
| 2009/0148661 A1 | 6/2009 | Stroebech et al. | |
| 2009/0149567 A1 | 6/2009 | Lam et al. | |
| 2009/0216169 A1 | 8/2009 | Hansen et al. | |
| 2009/0234313 A1 * | 9/2009 | Mullejeans | A61B 5/107 604/338 |
| 2009/0306571 A1 | 12/2009 | Lam et al. | |
| 2010/0016820 A1 | 1/2010 | Lam et al. | |
| 2010/0113999 A1 | 5/2010 | Lam et al. | |
| 2010/0114045 A1 * | 5/2010 | Cramer | A61F 5/445 604/338 |
| 2010/0191201 A1 | 7/2010 | Bach et al. | |
| 2010/0191204 A1 | 7/2010 | Bach et al. | |
| 2010/0198176 A1 | 8/2010 | Stroebech et al. | |
| 2010/0204664 A1 * | 8/2010 | Bach | A61F 5/445 604/344 |
| 2010/0204665 A1 | 8/2010 | Stroebech et al. | |
| 2010/0217215 A1 * | 8/2010 | Lykke | A61F 5/4404 604/344 |
| 2011/0040269 A1 | 2/2011 | Cline | |
| 2011/0125115 A1 | 5/2011 | Anders et al. | |
| 2011/0213321 A1 * | 9/2011 | Fattman | A61F 5/448 604/344 |
| 2011/0213322 A1 * | 9/2011 | Cramer | A61F 5/443 604/344 |
| 2011/0245789 A1 * | 10/2011 | Buus | A61F 5/443 604/344 |
| 2012/0283678 A1 * | 11/2012 | Nguyen-DeMary | A61F 5/441 604/337 |
| 2015/0088082 A1 * | 3/2015 | Lykke | A61F 5/4404 604/344 |
| 2015/0320585 A1 * | 11/2015 | Fattman | A61F 5/445 604/344 |

FOREIGN PATENT DOCUMENTS

| | | | |
|---|---|---|---|
| CN | 102655827 A | 9/2012 | |
| CN | 105163694 A | 12/2015 | |
| DE | 3017989 A1 | 11/1981 | |
| EP | 0272816 A2 | 6/1988 | |
| EP | 0413250 A1 | 2/1991 | |
| EP | 0882437 A2 | 12/1998 | |
| JP | 2013512004 A | 4/2013 | |
| JP | 2015536200 A | 12/2015 | |
| WO | WO-0044324 A1 | 8/2000 | |
| WO | WO-2005048891 A1 | 6/2005 | |
| WO | WO-2007128320 A2 | 11/2007 | |
| WO | WO-2008124716 A2 * | 10/2008 | A61F 5/445 |
| WO | WO-2008124717 A2 | 10/2008 | |
| WO | WO-2010060116 A1 | 5/2010 | |
| WO | WO 2014/081889 A1 | 5/2014 | |

OTHER PUBLICATIONS

New Zealand Patent Application No. 709028 second Examination Report dated Sep. 11, 2017.
Japanese Patent Application No. 2015-543150 Office Action dated Sep. 26, 2017.
Chinese Patent Application No. 201380070932.7 Office Action dated May 5, 2016.

(56) References Cited

OTHER PUBLICATIONS

European Patent Application No. 13856156.8 Supplementary European Search Report dated Oct. 31, 2016.
New Zealand Patent Application No. 709028 First Examination Report dated Jan. 25, 2017.
PCT/US2013/071098 International Preliminary Report on Patentability dated May 26, 2015.
PCT/US2013/071098 Written Opinion dated Feb. 26, 2014.
PCT/US2013/071098 International Search Report dated Feb. 26, 2014.
Japanese Patent Application No. 2015-543150 Decision of Rejection dated Mar. 5, 2019.
Japanese Patent Application No. 2015-543150 Office Action dated Mar. 13, 2018.
New Zealand Patent Application No. 709028 Further Examination Report dated Jan. 12, 2018.

\* cited by examiner

ONE PIECE OSTOMY POUCH ENHANCEMENTS

CROSS-REFERENCE

This application is a U.S. National Phase of International Application No. PCT/2013/071098, filed on Nov. 20, 2013, which claims the benefit of U.S. Provisional Application No. 61/728,581 filed on Nov. 20, 2012, entitled "One Piece Ostomy Pouch Enhancements," each of which are incorporated herein by reference in their entireties.

BACKGROUND OF THE INVENTION

Numerous medical conditions may require ostomy surgery resulting in the creation of a fecal or urinary stoma and the patient will eliminate waste into a container attached to their abdomen. This container is typically a bag or pouch that is attached to the body around the stoma by a wafer of bioadhesive called a skin barrier for its ability to protect the peristomal skin from stomal effluent. It is desirable to improve on the design of ostomy devices and pouches.

SUMMARY OF THE INVENTION

Provided herein are ostomy devices, methods for the manufacture of such devices and the use of such devices. In one embodiment, an ostomy pouch comprising an adhesive collar to secure the pouch around the stoma is provided herein, wherein the adhesive is exposed to the inside of the pouch for fitting around the stoma, wherein the pouch comprises a release coated surface to allow manipulation of the adhesive through the pouch, and to prevent blocking of the pouch during storage or use.

In one embodiment, an ostomy pouch comprising an adhesive collar is disclosed herein that is 'heart shaped' to increase adhered area in the 3 and 9 o'clock positions, and reduced adhered area at the top section.

In yet another embodiment, an ostomy pouch is provided herein comprising an adhesive collar that is 'heart shaped' to increase adhered area between the 3 and 9 o'clock positions, including the 6 o'clock position, and reduced adhered area at the top section.

In still another embodiment, an ostomy pouch is disclosed herein comprising a stoma viewing mechanism including a partially or totally opaque sheet of material on a front panel that has more than about 50% of its perimeter detached from the pouch. In some embodiments, the ostomy pouch is provided wherein the partially or totally opaque sheet of material that has more than about 65% of its perimeter detached from the pouch.

In some embodiments provided herein, an ostomy pouch may be partially or totally opaque sheet of material that has more than about 80% of its perimeter detached from the pouch.

In yet other embodiments, an ostomy pouch is provided wherein the partially or totally opaque sheet of material reveals more than 60% of its initially covered pouch area when manually manipulated to a stoma viewing position by 2 or fewer digits, for example a finger and thumb.

In still other embodiments, an ostomy pouch is provided wherein the partially or totally opaque sheet of material that reveals more than 70% of its initially covered pouch area when manually manipulated to a stoma viewing position by 2 or fewer digits, for example a finger and thumb.

In one embodiment, an ostomy pouch is provided wherein the stoma viewing mechanism comprising a partially or totally opaque sheet of material that reveals more than 75% of its initially covered pouch area when manually manipulated to a stoma viewing position by 2 or fewer digits, for example a finger and thumb.

In some embodiments, an ostomy pouch is provided herein having a stoma viewing mechanism which can also conceal and or hide the stoma and the pouch contents as needed.

In yet other embodiments, a stoma viewing mechanism is provided comprising a flap that is held closed by adhering to the underlying pouch via a pressure sensitive adhesive, Velcro, hook and loop, or a sleeve mechanism. In still other embodiments, a stoma viewing mechanism is provided herein comprising a flap that is held closed by the flap that includes partially or is entirely comprised of either the hook or the loop portion of a hook and loop or hook and hook fastening system, and the pouch film or comfort panel itself comprises the other half of the closure system, i.e. either the opposing hook or loop, or where the pouch film or comfort panel includes partially or is entirely comprised of either the hook or the loop portion of a hook and loop or hook and hook fastening system, and the flap itself comprises the other half of the closure system, i.e. either the opposing hook or loop.

In some embodiments, a controlled evacuation appliance is provided herein, wherein the controlled evacuation application provides, alternatively or additionally,
   a. an aperture that surrounds the stoma;
   b. attaches to the skin surrounding the stoma by means of an adhesive coupling;
   c. incorporates a pouch for collecting effluent, whereby the pouch is made of thin, flexible plastic, is non-elastic, is folded into a small volume on the device, and can be deployed for collection of waste at the discretion of the wearer;
   d. utilizes stool trapped within the internal volume of the device as a sealing means to resist outflow of additional effluent from the stoma;
   e. incorporates a cover to contain the pouch and protect the device, wherein the cover is made from a flexible, non-elastic material; and/or
   f. incorporates a vent path for flatus that is released from the stoma.

In some embodiments, the appliances provided herein comprises a pouch, whereby the pouch is folded longitudinally, and then rolled into a compressed format. In some embodiments, the pouch is folded longitudinally, and then folded in layers against the outer surface of the device. In other embodiments, the pouch is folded longitudinally, and then folded successively latitudinally to its final compressed shape. In yet other embodiments, the pouch is folded longitudinally, and then folded successively diagonally to its final compressed shape. In some embodiments, the capacity of the pouch is between 100 ml and 750 ml.

In still other embodiments, a cover is included in the controlled evacuation appliances provided herein whereby the cover is made from a plastic film. In some embodiments, the cover is made from a textile. In still other embodiments, the cover at least partially covers and restrains the stored pouch. In yet other embodiments, the cover is attached at two or more points to the attachment means.

In some embodiments, a vent path is provided in the controlled evacuation appliances provided herein, wherein the vent path is protected by a porous element. In some embodiments, the vent path is defined by a film baffle that directs gas flow.

In other embodiments, the controlled evacuation appliances provided herein incorporate an inflatable seal that contacts the stoma.

In some embodiments, a controlled evacuation appliance is provided herein, wherein the controlled evacuation application provides, alternatively or additionally
  a. incorporates an aperture that surrounds the stoma;
  b. removably attaches to a skin barrier ostomy wafer by means of a coupling
  c. incorporates a pouch for collecting effluent, whereby the pouch is made of flexible plastic, is non-elastic, is folded into a small volume on the device, and/or can be deployed for collection of waste at the discretion of the wearer;
  d. utilizes stool trapped within the internal volume of the device as a sealing means to resist outflow of additional effluent from the stoma;
  e. incorporates a cover to contain the pouch and protect the device, wherein the cover is made from a flexible, non-elastic material; and/or
  f. incorporates a vent path for flatus that is released from the stoma.

In some embodiments, the controlled evacuation appliances incorporates an inflatable seal that contacts the stoma.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1a. illustrates a straight cut through pouch front panel for stoma viewing; 1b. illustrates overlapping front panels for stoma viewing; 1c. illustrates curved cut through pouch front panel for stoma viewing.

Figure 2:
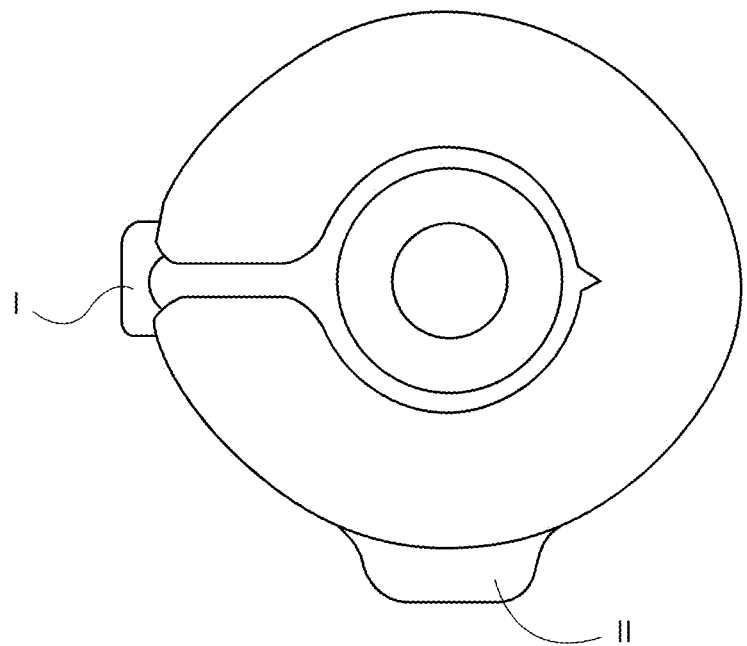

FIG. 2: illustrates an adhesive collar with segmented release liner as one embodiment as disclosed herein.

Figure 3:
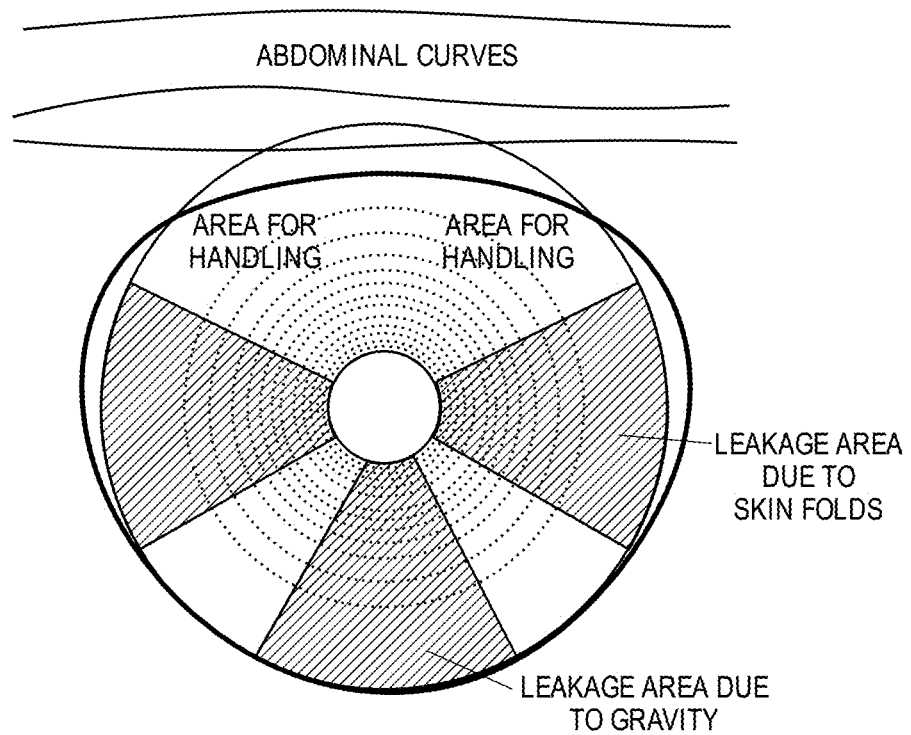

FIG. 3: illustrates a "heart-shaped" adhesive collar as another embodiment as disclosed herein, as compared to a circular adhesive collar.

Figure 4:
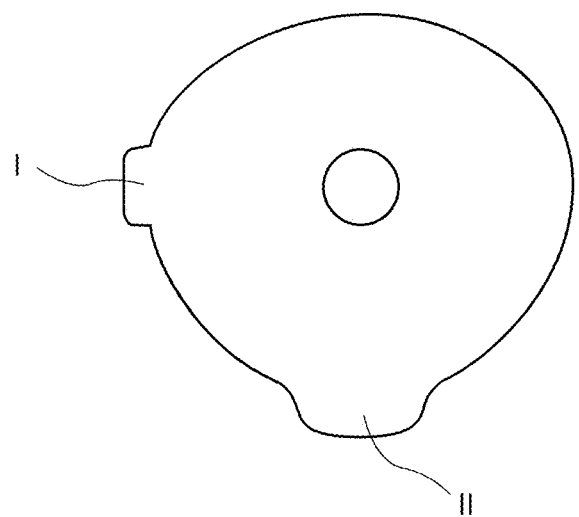

FIG. 4: illustrates a "heart-shaped" adhesive collar and segmented release liner as yet another embodiment as disclosed herein.

Figure 5:
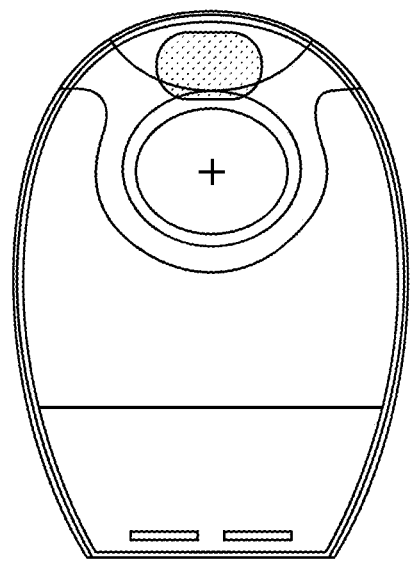
Figure 6A:
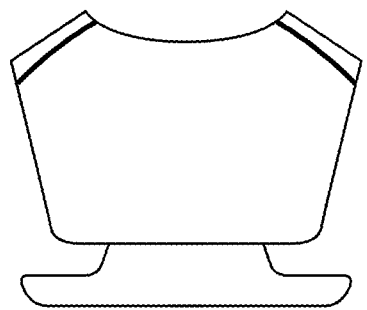
Figure 6B:
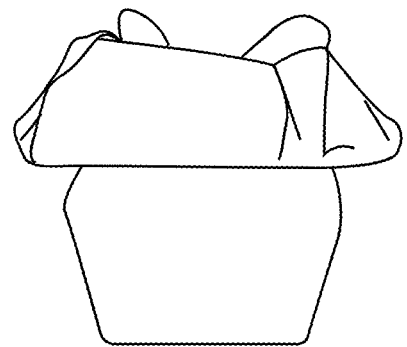
Figure 6C:
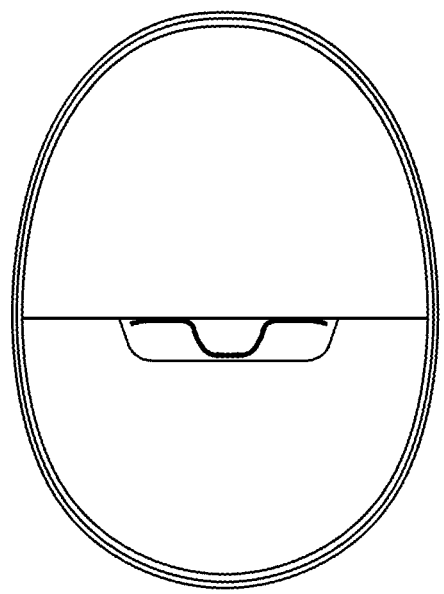
Figure 6D:
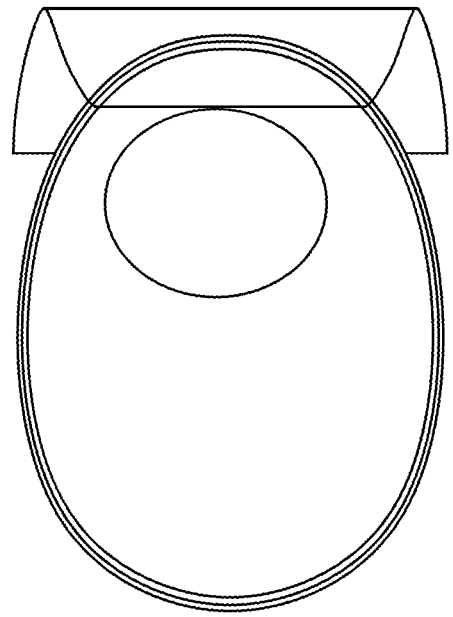

FIG. 5: illustrates flap in front panel for stoma viewing as an additional embodiment as disclosed herein.

FIG. 6: panels a-d illustrate a partly detachable flap for viewing a stoma.

Figure 7:
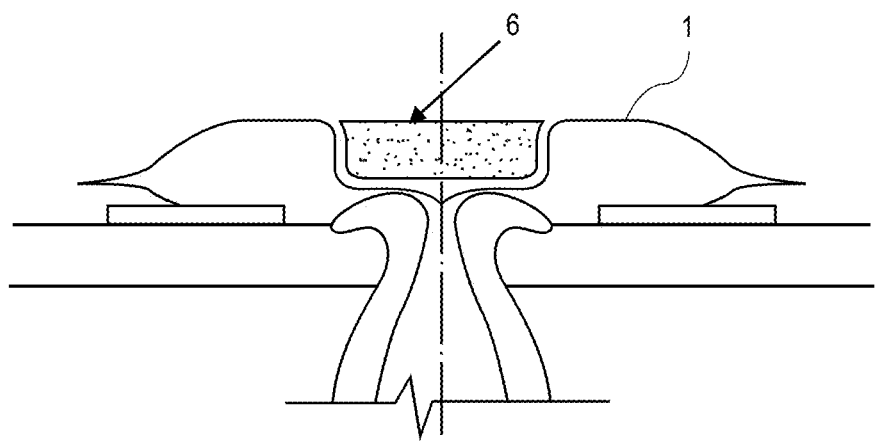

FIG. 7: illustrates an inflatable seal incorporated in or into the outer pouch wall (1).

Figure 8:
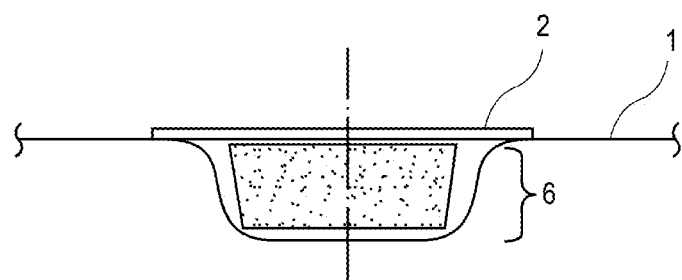

FIG. 8: illustrates an outer panel (2) enclosing the inflatable seal (6).

Figure 9:
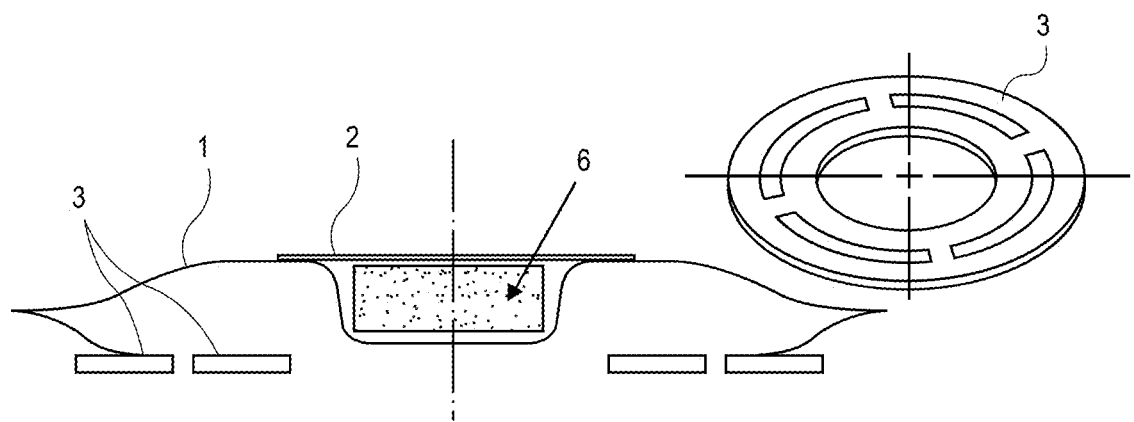

FIG. 9: illustrates a coupling member that may be employed with the methods and devices disclosed herein comprising at least one contiguous adhesive element.

Figure 10:
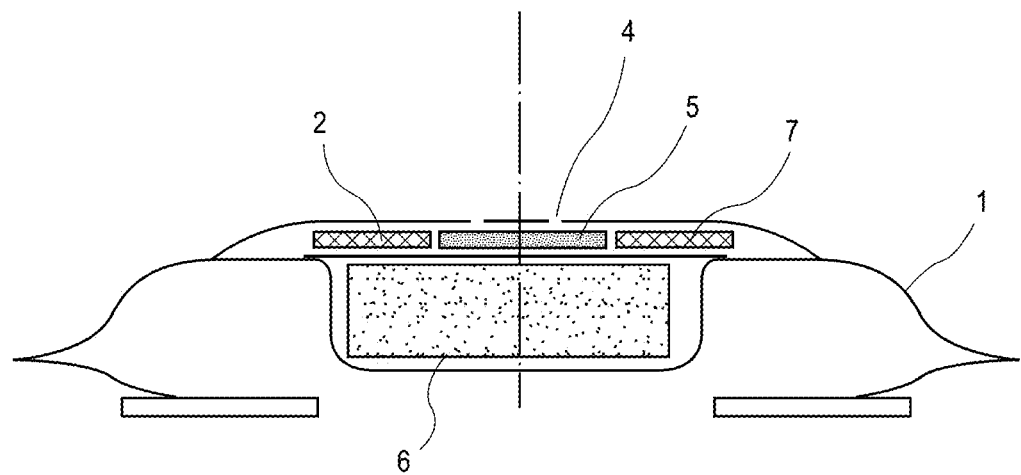

FIG. 10: illustrates the use of a layer of open cell foam in a pre-filter (7) to protect an ostomy device including a filter and vent.

Figure 11:
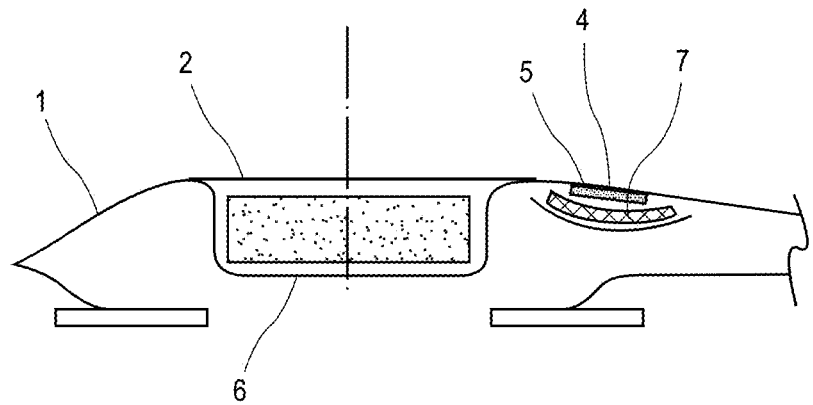

FIG. 11: illustrates an alternative embodiment of a vent (4) and filter (5) that could be located in the head space of the pouch or in the pouch itself.

Figure 12:
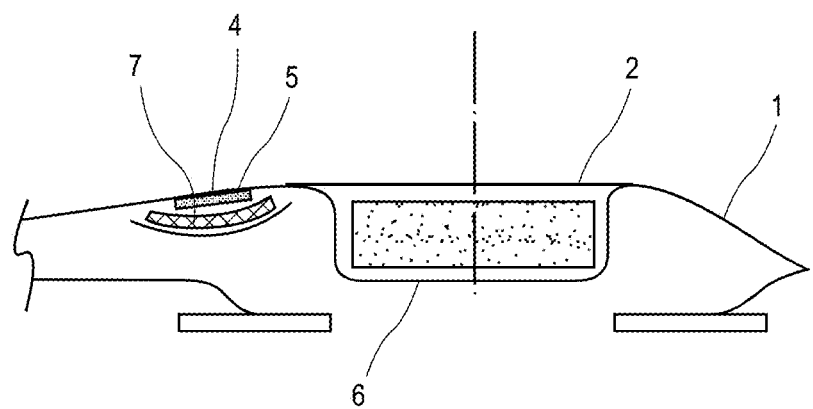

FIG. 12: illustrates illustrates an alternative embodiment of a vent (4) and filter (5) that could be located in the head space of the pouch or in the pouch itself.

Figure 13:
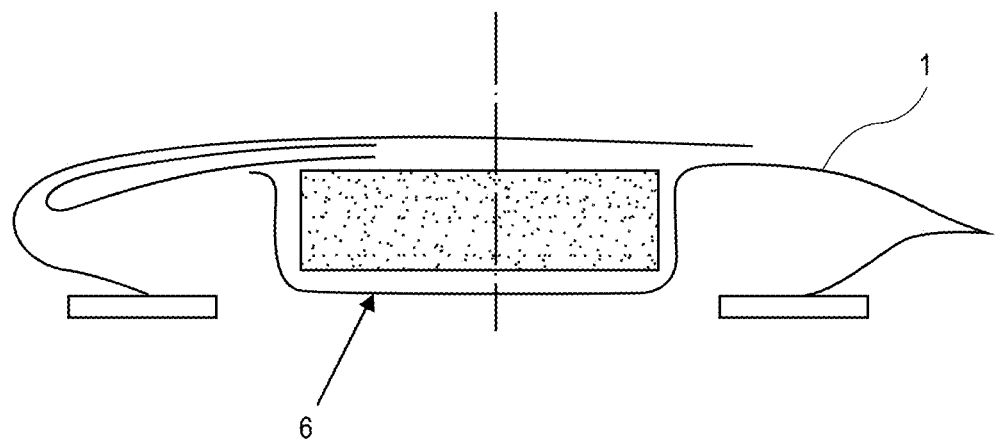

FIG. 13: illustrates folding of the pouch in alternate layers across the outer face of the device.

Figure 14:
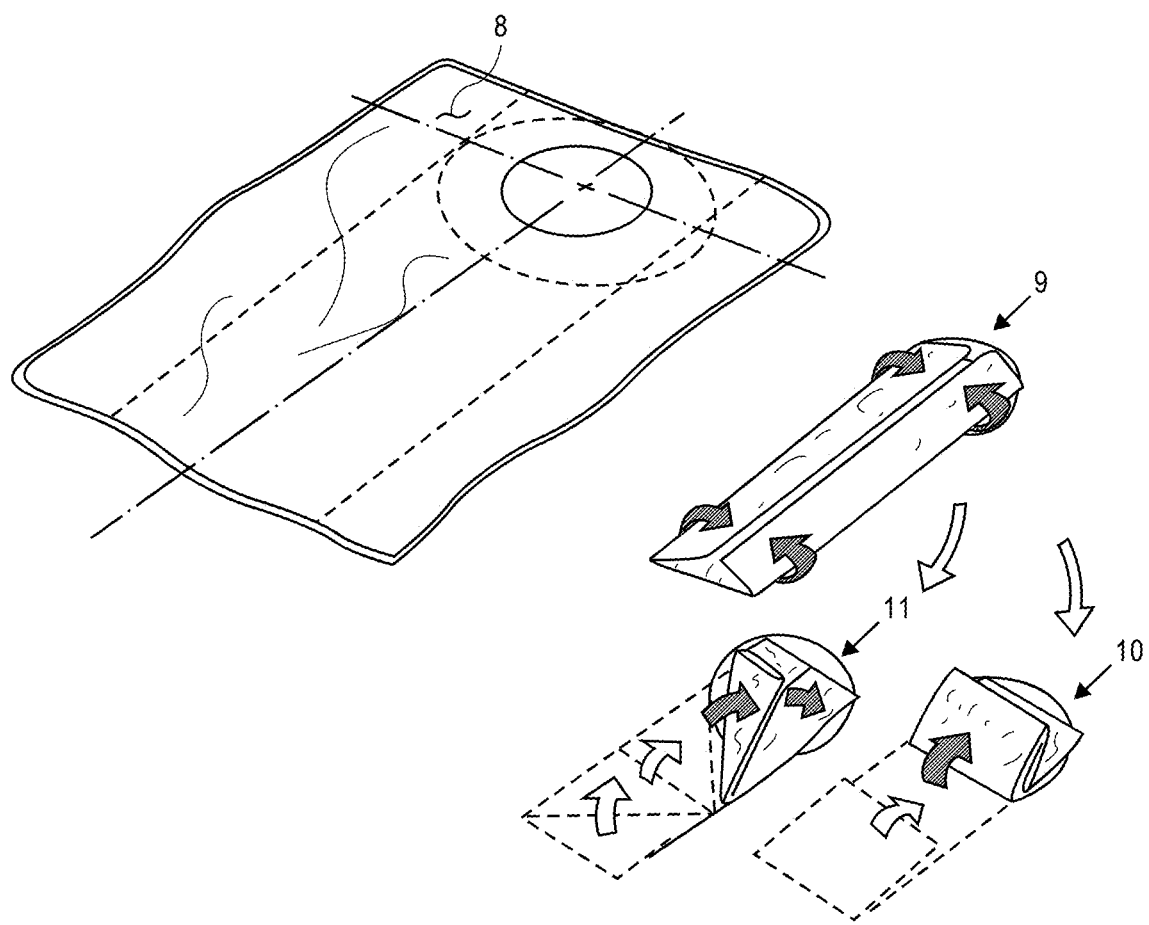

FIG. 14: illustrates alternative folding arrangements may be employed, including but not be limited to, creating longitudinal folds (9) in the pouch, followed by latitudinal folds (10) or diagonal folds (11).

Figure 15:
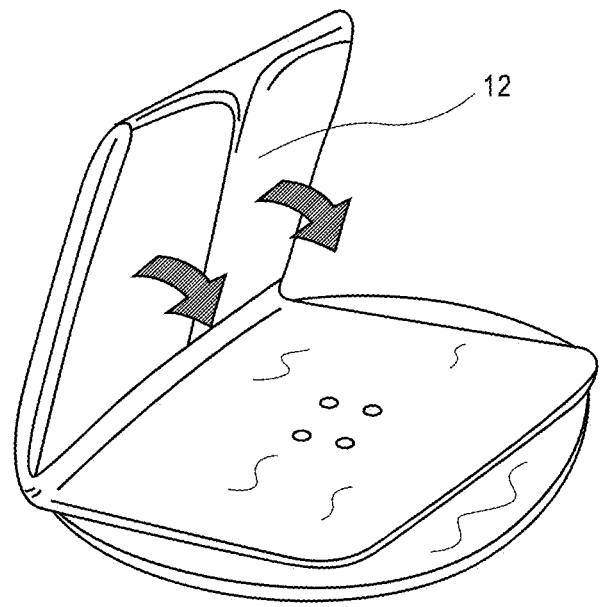

FIG. 15: illustrates an embodiment in the disclosure incorporating longitudinal pleats (12) in the outer pouch film to provide a flow path, when folded, for gas out of the device.

Figure 16:
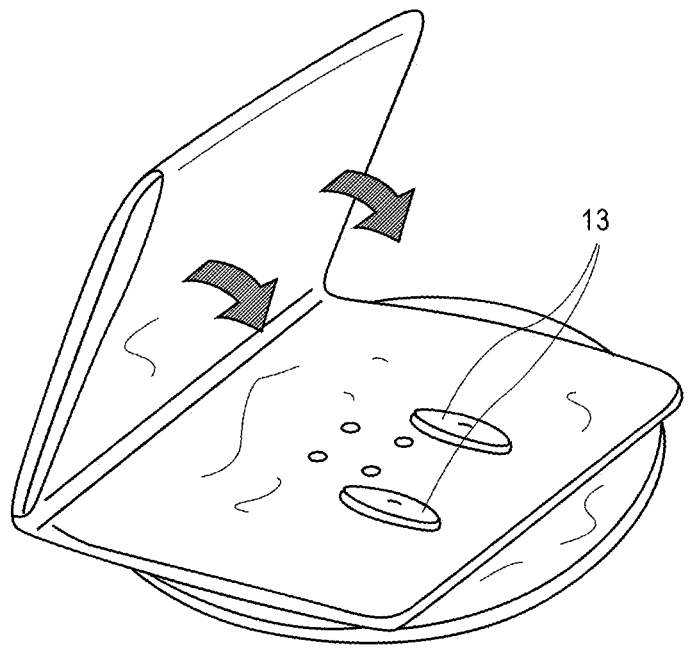

FIG. 16: illustrates features (13) formed in at least one element disclosed herein covering the filter to provide a flow path out of the filter.

Figure 17:
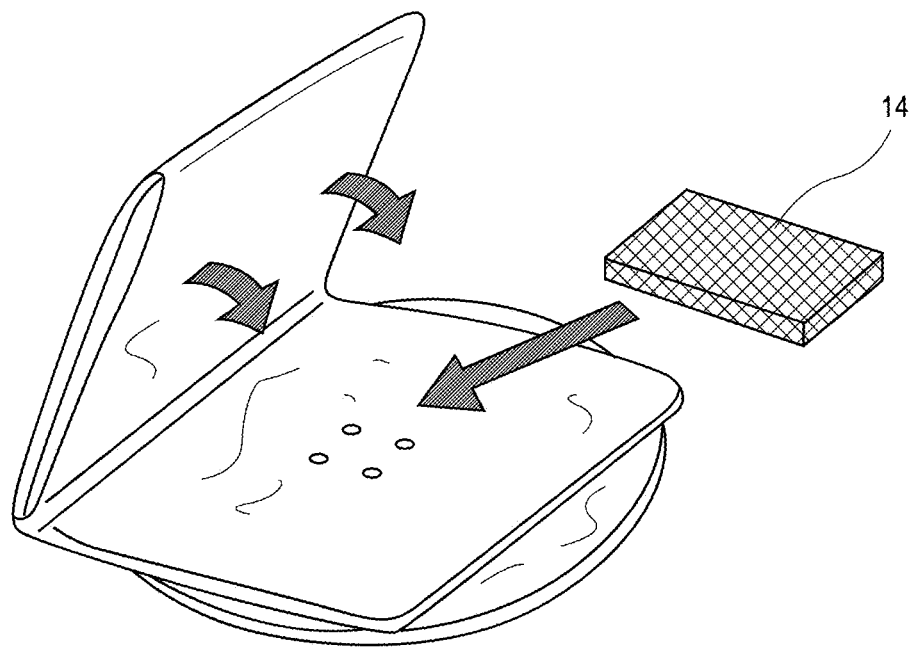

FIG. 17: illustrates the use of at least one additional element to act as a spacer between the face of the device and the folded pouch to provide a flow path.

Figure 18:
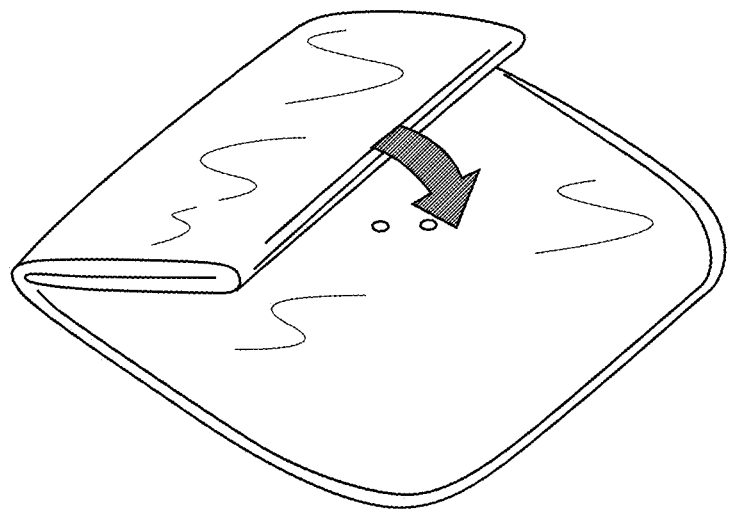

FIG. 18: illustrates alternative methods of altering folding the pouch to leave the vent path at least partially unobstructed.

Figure 19:
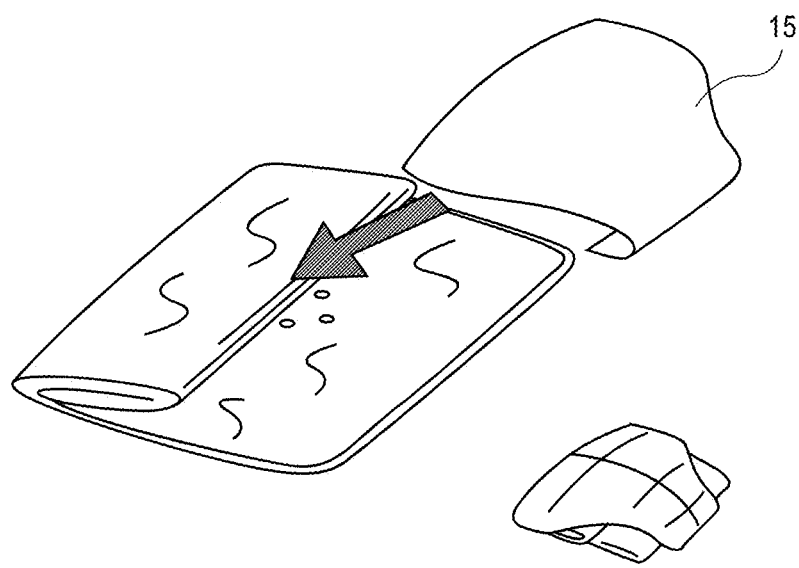

FIG. 19: illustrates the incorporation of a film element (15) to cover the ostomy devices disclosed herein.

Figure 20:
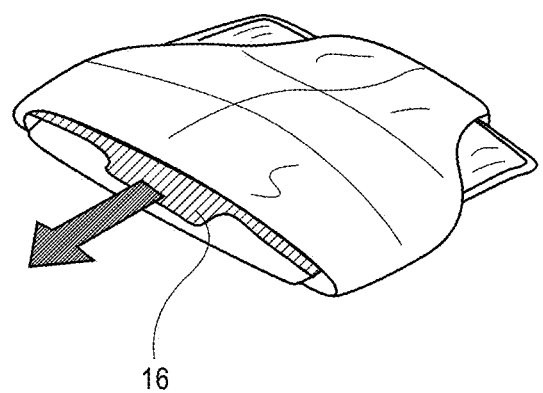

FIG. 20: illustrates pulling a film out from a cover of the ostomy devices disclosed herein, by means of a protruding tab (16) or other means of engaging the pouch, which may allow the pouch to be unfolded and fill with stool as the seal is pulled away from the stoma.

Figure 21:
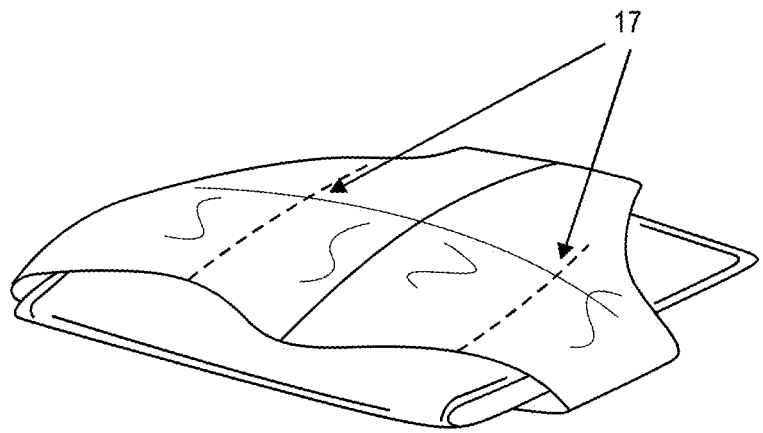

FIG. 21: illustrates the insertion of a finger under a cover of the ostomy devices disclosed herein and lifting, wherein the cover could be intentionally torn to release the folded pouch.

Figure 22:
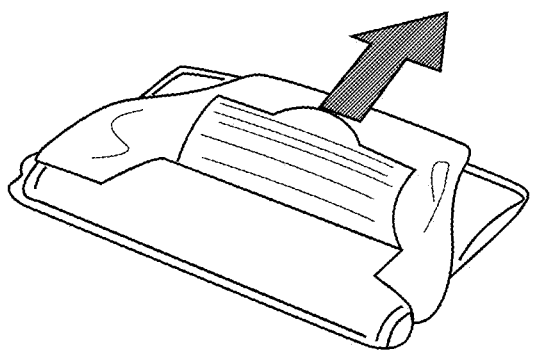

FIG. 22: illustrates the insertion of a finger under a cover of the ostomy devices disclosed herein and lifting, wherein the cover could be intentionally torn to release the folded pouch.

Figure 23:
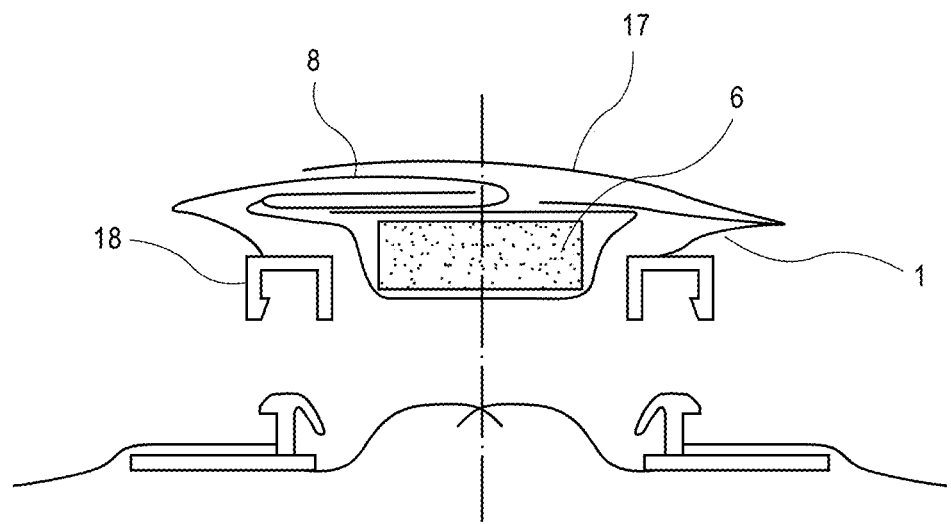

FIG. 23: illustrates the removal of a two-piece version of the devices disclosed herein, with a final step of removing the device from the ostomy wafer and leaving the ostomy wafer in place.

Figure 24:
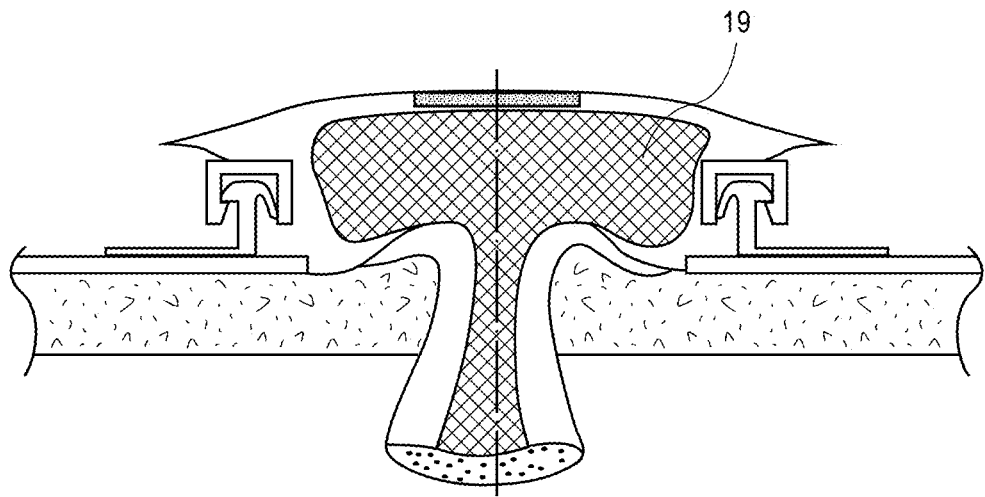

FIG. 24: illustrates the stool expelled from the stoma that becomes trapped above the stoma and effectively functions as a temporary seal.

Figure 25:
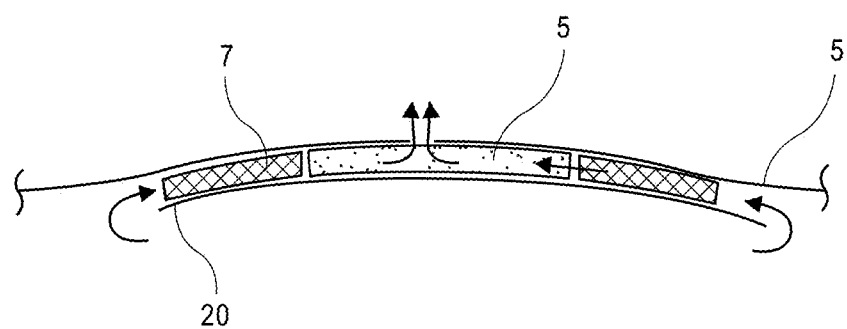

FIG. 25: illustrates a baffle which could be fixed in place, by means of welding, adhesives, or discrete fasteners, so that access to a prefilter would be limited to an inwardly radial path.

DETAILED DESCRIPTION OF THE INVENTION

Numerous medical conditions may require ostomy surgery resulting in the creation of a fecal or urinary stoma and the patient will eliminate waste into a container attached to their abdomen. This container is typically a bag or pouch that is attached to the body around the stoma by a wafer of bioadhesive called a skin barrier for its ability to protect the peristomal skin from stomal effluent. When the collecting bag is removably attached to wafer via a coupling mechanism, it is referred to as a two-piece device. When the wafer and the bag are permanently attached to each other, the device is referred to as a one-piece device, or a one-piece pouch, or sometimes simply as a pouch.

A controlled evacuation device incorporating a collection pouch that can be deployed to allow release and capture of effluent while the device is being worn has been described in Patent Application US2012/0283678. This document describes devices and methods, particularly ostomy or controlled evacuation devices that can be worn to achieve fecal continence for several hours. And when the need to evacuate occurs, the collection pouch can be deployed to allow capture of effluent for many additional hours until the wearer desires to remove the device. Such an invention offers the wearer temporary continence. But it also can be worn after effluent is released, by means of the pouch that can be deployed for storage of released effluent.

Ostomy pouches are typically formed by sealing two panels of odor-proof film about a perimeter, the body side pouch panel and the front-side pouch panel. This sealed perimeter is sometimes referred to as the pouch outline weld reflecting a commonly used heat sealing process. The body side pouch panel typically includes a means to attach to a skin barrier, and the skin barrier and body-side pouch panel having a co-located opening for receiving the stoma. Because the pouch's odor proof plastic films will adhere to skin should it become wet with perspiration the pouch is typically surrounded with a layer of softer fabric material, for example a layer of nonwoven fabric, which may be cut and welded together with the pouch film panels. Pouches typically have a deodorizing filter to allow deodorized flatus to escape the pouch volume and maintain a flat, discrete wear.

The shape of the stoma typically changes from what was surgically created and if these changes are non-uniform or asymmetrical then a need arises to customize the opening in the skin barrier through which the stoma protrudes into the pouch. It has been found in several human studies that the fit of the wafer around the stoma significantly impacts the ability of the skin barrier to protect peristomal skin. The resultant skin damage from an improperly fitted ostomy skin barrier directly impacts the quality of life for the ostomate. It has further been learned that molding the skin barrier to the shape of the stoma improves the fit of the appliance to the stoma. For these reasons it is desirable to include moldable wafer technology in the design of one piece pouches.

Ostomates require a pouch immediately following surgery and essentially for the lifetime of the stoma (note that the surgery can be reversed). As a result the pouch design may not be optimum in all circumstances. For example, post operatively there are various early complications that may impact the stoma and patient including ischemia, stomal retraction, bleeding, and mucocutaneous separation. For these reasons it is desirable to visualize the stoma arid pouch contents immediately post operatively. Later complications may also benefit from this visualization. For these reasons a clear or transparent pouch is often selected for use immediately post operatively so that the care giver can readily observe the stoma and pouch contents.

In contrast to the above situation it has been found that many patients recovering from recent ostomy surgery do not wish to see their stoma. The site of the protruding stoma and presence of waste outside the body can be unsettling and for this reason the ostomate will soon substitute an opaque pouch for the clear post operation pouch as they return to normal activities in the community.

Figure 1B:
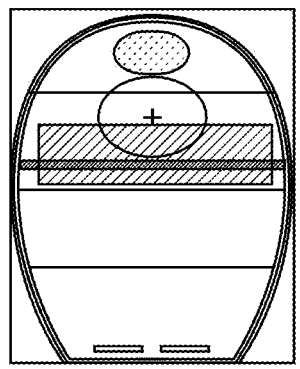
Figure 1C:
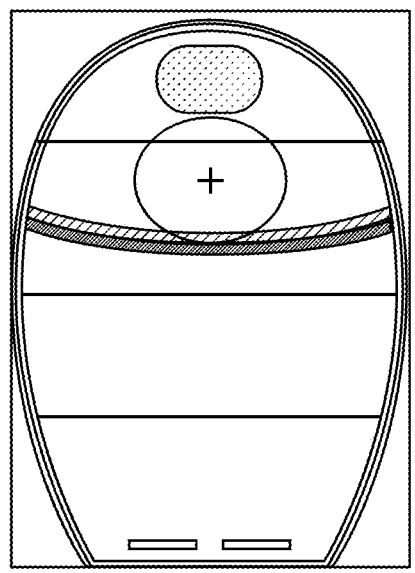

To accommodate these different requirements ostomy pouch manufacturers make both transparent and opaque pouches. Recently pouches have also been designed with an additional front panel to create a stoma observation mechanism comprising a flat, opaque sheet that can be lifted up or pulled apart to reveal a transparent undersheet that comprises the front panel of the ostomy pouch proper. See, e.g., FIG. 1a-c. In this way the stoma and pouch contents may be observed or hidden by the same pouch design. More commonly the design of the observation mechanism includes a split in the opaque sheet created by cutting through the layer of comfort material on the front of the pouch in an area where the stoma can be viewed. Initially this split may be weakly attached in a closed position by an incomplete split, for example perforations. By doing so the comfort panel remains flat during processing, and ostomates who do not wish to view their stoma are not concerned that the split may accidentally open. To view the stoma any perforations that may be present are broken so that the opaque sheet can be pulled apart. If no perforations are used then the sheet is simply lifted. The stoma observation mechanisms believed to include the entire prior art have designs that are either "straight through", approximately linear aligned laterally across the face of the front of the pouch, or curved of various degrees of curvature, rounded up like the bottom half of a clock face. In all cases the mechanism includes a design wherein the opaque sheet has a significant proportion of its perimeter trapped in the outline weld of the two odor proof pouch panels.

It has been discovered that several drawbacks exist with the state of the art for stoma observation mechanisms comprising opaque sheets covering the front pouch panel.

When the flat opaque sheet is attached to the pouch at the pouch outline weld as part of the seal between the two pouch panels it cannot be easily opened far enough to reveal all of the stoma without jeopardizing the integrity of the pouch seal. Additionally, the pouch contents are extremely difficult to observe because the sheet cannot be lifted far enough to see to the bottom of the pouch. This situation is particularly difficult when the opaque sheet is lifted up from the bottom because the ostomate is normally looking down from above the pouch, and the lifted opaque sheet will bunch up directly above the viewing area. Moreover the ostomates hand will be holding the opaque sheet and so will also obstruct viewing.

This situation illustrates further drawbacks that the ostomate will realize when trying to view the stoma through the split opening during pouch fitment. On a flat abdomen the ostomate may be able to directly see the stoma during fitment of the skin barrier. However, sometimes the stoma cannot be observed directly as a result of an interceding body part like a protruding abdomen or breast. In this case fitment of the wafer to the stoma is accomplished by viewing the stoma reflection in a mirror. Fitment is aided when the mirror is oriented so that the stoma is viewed through the front pouch panel. For transparent pouches this method of fitment is commonly used. In the case where the stoma is obscured by an opaque sheet, when a hand is required to keep that sheet open then that hand is unavailable for fitment of the skin barrier. Additionally, the act of pulling open the split can cause the wafer to become ruffled or otherwise render it not flat as required for proper application to the peristomal skin.

Stoma viewing mechanisms comprised of split opaque sheets have several additional limitations. First, when a perforated sheet is used, because the split film is initially weakly attached by an incomplete cut, the ostomate must physically separate the split. This can be difficult for some ostomates who often have limited manual dexterity and visual acuity. Second, the act of "breaking" part of the pouch creates apprehension about whether the pouch may be inadvertently damaged by the procedure. Third, once it has been opened the sheet may not readily close to the same flatness as prior to opening. As a result the opened split sheet renders the device less discrete and more likely to catch on clothing, increasing the problem. The possibility also exists that the opened area may capture something from the surrounding environment, for example water from a shower or pool, causing inconvenient wetness, uncomfortable sag, and additional weight in the pouch. Finally, other pouch components that may be attached to the front pouch panel, for example the pouch filter, are impacted by the requirement that they be compatible with the presence of the opaque split sheet.

It addition it may be desirable to provide these functions in other configurations that can be attached worn as a one-piece appliance or as a two-piece appliance that can be worn in conjunction with a separate ostomy wafer, to which the device can be removeably attached to the wearer.

In some embodiments provided herein, an ostomy appliance of the present invention provides a protective release liner design and a novel collar design.

As mentioned above, the bioadhesive, which is part of the ostomy appliance, secures the collection bag or pouch to the human body. This bioadhesive is protected with a silicone release-coated film or release liner. Most products that are available to the ostomates today use a single release liner which is removed as one-piece prior to use. However, it has been discovered that many enterostomal nurses teach their patients to apply the pouch by cutting their stoma shaped pattern into the skin barrier and then folding it in half horizontally, by folding down the top half of the skin barrier so that it is doubled over the bottom half of the skin barrier. The pouch, including the folded adhesive, is then held under the stoma and raised until the skin barrier contacts the peristomal skin adjacent to the bottom half of the stoma. The skin barrier is then unfolded and placed against the peristomal skin all around the stoma including now the top half. This technique allows the wearer to better visualize application of the skin barrier around the stoma to ensure proper placement for optimum skin protection. To facilitate this technique the present invention allows the release liner to be removed in separate segments, including segments designed to assist folding the wafer, and to assist in estimating where the wafer is to be folded, including, for example, at the half-way point. In addition to the abovementioned situation for cut to fit wafers, in the case where the wafer will be molded to tilt the stoma shape, this design enables the release liner to be removed in segments to facilitate molding as well, for example when the adhesive section near the stoma has to be manipulated for better fit around the stoma by hands, and so removing the release liner entirely could cause contamination of the skin adhering area during manipulation of the central area.

To address this issue, the present invention includes a segmented release liner design (FIG. 2) which is removed in following steps:

Step 1: Release liner tab marked "I" is removed first.
Step 2: The exposed adhesive around the central starter hole is manipulated to increase the hole size to fit around stoma.
Step 3: Lift tab marked "II" and fold in half.
Step 4: Attach exposed bottom half of adhesive collar to bottom portion of stoma.
Step 5: Remove release liner completely by pulling tab marked "2" and attach the adhesive around top half of stoma.

Yet another aspect included herein is the shape of the adhesive collar that holds the collection bag or pouch in place during use. It is known that typically, leakage occurs due to skin folds at the 3 and 9 o clock positions on the adhesive collar, and due to gravity it leaks through the bottom as shown in FIG. 3.

The heart-shaped adhesive collar (FIG. 4) provides additional adhesive around the stoma between the 3 o'clock and 9 o'clock positions, including also the 6 o'clock position, thus reducing the possibility of leakage that occurs at these positions. Additional adhesive or reinforcement of adhesive around the stoma could also occur at other positions, including at or near at least one of the positions of 3 o'clock, 4 o'clock, 5 o'clock, 6 o'clock, 7 o'clock, 8 o'clock or 9 o'clock.

The segmented release liner comprises a flexible film or paper which is coated with silicone or other release coatings. The film is made of polyethylene, polypropylene, polyester, EVA, polyamide, polycarbonate, or a combination thereof. The heart-shaped adhesive collar may be used in conjunction with the segmented release liner as yet another embodiment of the controlled evacuation devices provided herein. FIG. 5.

It has been discovered that the failings of the prior art can be alleviated by dissociation, i.e. partial, near or total disassociation of the split sheet from the outline weld of the pouch. In an example of the preferred embodiment shown below the sheet is in the form of a flat "flap" of opaque sheet that may have one or more layers. It is substantially detachable from the pouch outline weld to the extent that it moves freely and independent of the body of the pouch. The dissociation from the outline weld is to an extent where the sheet or flap can be easily manipulated by hand to reveal a significant proportion of the area of the pouch that it initially covered prior to manipulation. Visualization of both the stoma and pouch contents is greatly improved compared with split opening opaque sheet designs.

Another improvement is realized when sufficient freedom of movement created in the detached sheet such that it is enabled to be maintained in a stoma viewing position, or "open", without the need to be continuously contacted by an opening force or mechanism, for example hand contact. One embodiment provided herein is to fold the flap over the top of the pouch. In this way hands are freed to be available for proper wafer fitment and without obstructing the view of the stoma. Components that may be used to secure the flap in an open or closed position include layers of pressure sensitive adhesive mechanical interlocking or interfering mechanisms or other frictional restraints. For one piece pouches with moldable skin barriers it becomes possible to manually manipulate the molding adhesive with one or both hands. Molding and other fitment processes or adjustments can be accomplished by indirectly contacting the adhesive while pressing on the transparent front pouch panel. Because this manipulation can be easily visualized it further improves the fitment procedure and betters the quality of life for ostomates by preventing painful and irritating peristomal skin damage.

Release Coated Inner Pouch Film

Another aspect included herein is the fitment through the front pouch panel, which is further improved by including a release coated sheet between the front pouch panel and the adhesive surface internal to the pouch. The release coated sheet prevents adhesion between the pouch panel and the surface of adhesive being molded. A further benefit is that the release coated surface aids in release of pasty stomal effluent from the pouch front panel and causing it to slide down the pouch more easily. Bulking of pasty fecal effluent stuck to the pouch front panel is not discrete, and when effluent falls to the bottom of the pouch wearing the pouch is more comfortable for the pouch user. It also greatly benefits pouch function. Effluent pasted to the pouch panel opposite the stoma can adhere the two pouch panels together, causing them to "block" and effectively close off some volume of the pouch. Thus the pouch is prevented from readily accepting additional effluent. If new effluent cannot enter the pouch the pouch filter may become fouled with effluent. The pathway for flatus to find the filter may be obstructed and the filter will not receive and deodorize flatus. Other issues may include effluent forced under the skin barrier, either by peristaltic excretion or pneumatically by force of unvented flatus.

Because this invention enables a significant proportion of the initially covered area to be easily exposed anything that may be captured from the environment, for example water from a pool or shower, can be easily untrapped and removed or dried.

An additional benefit is that operations that may be done to the front of the pouch, for example during pouch manufacture, are made easier since the flap can be moved out of the way of the pouch front panel. The flap can be either attached during the welding of the pouch outline or in a later process step, improving process flexibility.

Because less distortion of the flap is required to view the stoma it is more flat when released or returned to its stoma hiding position, or "closed." The perception that the wearer may damage the pouch by tugging on perforations or otherwise distressing a sheet trapped in the pouch outline weld is eliminated. Since the sheet is less constrained it is more receptive to additional components that may be used to temporarily "lock" the sheet in the closed position. These components fit more easily on the pouch and are easier to manufacture. Additional components comprising a layer or layers of pressure sensitive adhesive; mechanically interlocking or interfering mechanisms, or other chemical or physical connections between the flap and the pouch body that are capable of maintaining the hiding sheet in a closed position against the frictional or shear forces of ordinary clothing and body movement are incorporated herein.

A further element of the preferred embodiment of the invention includes the ability to "tuck" at least some portion of the flap into the pouch front panel or a secondary front panel or the pouch comfort material layer wherein the flap may be secured or secreted in either open or closed position. See FIG. 6. In the picture above the flap can be manipulated in either direction, lifted or inverted, by folding it towards the pouch body and directing it through the opening between where it attaches to the pouch at the pouch outline weld. By tucking the flap into the opened area the stoma can be continuously visualized without the need for the flap to be constantly held out of the field of view. In this way the upper tuck "locks" the visualization mechanism in an open position for stoma viewing. Similarly, the flap may be manipulated into the down or closed position and any part of its edge inserted into a fold or an opening created adjacent to the flap perimeter in either the pouch front panel or a secondary front panel or the pouch comfort material layer wherein the flap may be secured or secreted in the closed position.

A stoma viewing mechanism comprising a flap that is held closed by adhering to the underlying pouch via a pressure sensitive adhesive, VELCRO®, hook and loop, or a sleeve mechanism. An especially preferred embosiment is that the flap includes partially or is entirely comprised of either the hook or the loop portion of a hook and loop or hook and hook fastening system, and the pouch film or comfort panel itself comprises the other half of the closure system, i.e., either the opposing hook or loop. Alternatively, another embodiment is that the pouch film or comfort panel includes partially or is entirely comprised of either the hook or the loop portion of a hook and loop or hook and hook fastening system, and the flap itself comprises the other half of the closure system, i.e., either the opposing hook or loop.

Controlled Evacuation Ostomy Device

A controlled evacuation ostomy device should perform three basic functions:

Prevent escape of effluent from the stoma or out of the device

Allow venting of gas that is released from the stoma

Allow for controlled capture of effluent that is released from the stoma

In addition to embodiments described in US Patent Application 2012/0283678, there are alternative means to achieve these functions. Embodiments provided herein improve the function of such devices, improving ease of use, broadening its scope of use, and reducing its manufactured cost.

In some embodiments, an inflatable seal is incorporated in or into the outer pouch wall (1), as seen in FIG. 7. In some embodiments, the inflatable seal may be employed to seal the surface of the outer wall of the pouch. Exemplary embodiments may include, for example, inflatable seals as described in U.S. Pat. No. 8,217,221, incorporated herein by reference for this disclosure. As such, it is possible to simplify the structure of the device by employing the outer pouch wall (1) as the sealing surface.

An outer panel (2) enclosing the inflatable seal (6) may also be used, as illustrated in FIG. 8. This panel may be made of flexible film or, alternatively, be made of a semi-rigid material or may be molded in a rigid material. In some embodiments, this panel may incorporate all appropriate fluid flow control elements. Exemplary embodiments may include fluid flow control elements as described in U.S. Pat. Nos. 7,347,844, 6,723,079, 8,092,437, 8,096,980, and US Patent Application No. 2011/0040269, incorporated by reference herein for this disclosure.

In some embodiments, a coupling member (3) may be employed comprising at least one contiguous adhesive element. It may be desirable in some cases to employ two or more elements, which may be concentric. See, e.g., FIG. 9. In some embodiments, the ostomy devices employing at least one contiguous adhesive element may benefit by the contiguous adhesive element acting as a "break" for undermining, or radial channeling, of effluent in a singular direction. Once the effluent encounters the break, the effluent in the ostomy device may be presented with a new and intact adhesive barrier to resist local channeling. In some embodiments, exemplary structures of contiguous adhesive elements may be found, for example, in US Patent Application No. 2012/0283678, incorporated by reference for this disclosure.

In yet other embodiments, the ostomy devices and methods disclosed herein may be able to effectively vent and deodorize gas that is released from the stoma in order to avoid build up of pressure in the bowel and in the device. See, e.g., FIG. 10. Such pressure could weaken the attachment between the adhesive wafer and the wearer's skin, potentially shortening the life expectancy of the device. Such pressure could also potentially cause discomfort for the wearer.

It is important that ostomy devices and methods disclosed herein incorporating at least one vent and one filter be prevented from clogging and fouling with effluent. Clogging of the vent path with effluent can prevent the device from venting, causing pressure build-up within the device. Fouling of the filter with the solid or liquid component of feces can destroy the filter's ability to deodorize. Protection of the vent and filter from clogging and fouling may be achieved by creating a broad vent path with multiple paths of access to the filter. This effect is enhanced by creating a tortuous path to the filter, so that if one path is blocked, many other paths are available for flow. One method of creating a tortuous path is to utilize a series of pleats or bumps formed in the film itself. Another method is to use a layer of open cell foam in a pre-filter (7) to protect the filter (see FIG. 10).

Such a vent (4) and filter (5) could be located above the inflatable seal (6) (see FIG. 10). Alternatively, it could be located in the head space of the pouch or in the pouch itself (see FIGS. 11 and 12).

In some embodiments, stowage of the pouch is included in the overall structure of the device. Folding and then rolling the pouch for storage at the bottom edge of the device has been previously described. In some embodiments incorporated herein, the pouch may be folded in alternate layers across the outer face of the device (see FIG. 13). Folding of the pouch results in a folded structure that is thin, does not place an unacceptable amount of localized stress on the pouch film, is easily unfolded, and which does not interfere with the flow of gas through the filter and vent system.

In some embodiments, alternative folding arrangements may be employed. These would typically involve, but not be limited to, creating longitudinal folds (9) in the pouch, followed by latitudinal folds (10) or diagonal folds (11) (see FIG. 14).

In some embodiments, flow of vented gas is facilitated out of the device, which can be achieved through several means. One such embodiment incorporates longitudinal pleats (12) in the outer pouch film to ensure that the film, when folded, provides a flow path for gas out of the device (see FIG. 15). In most, but not all embodiments, that flow path would include a filter, such as a matrix of activated carbon in a porous medium.

In yet another embodiment, incorporated herein are features (13) formed in the element, as detailed above, covering the filter to provide a flow path out of the filter (see FIG. 16).

In still another embodiment, disclosed here is the use of at least one additional element to act as a spacer between the face of the device and the folded pouch to provide a flow path for the effluent. This element can be, but would not be limited to, a stamped component, with or without raised features. In other embodiments, the element could also be made of a porous material, which includes but is not limited to such features as an open cell foam (14) (see FIG. 17).

In still another embodiment, included are methods of altering folding the pouch to leave the vent path at least partially unobstructed (see, e.g., FIG. 18). There are alternative means of altering folding the pouch. The object here is to leave the vent path at least partially unobstructed through the pattern of folding utilized.

In some embodiments, it is important to enclose the pouch to hold it in place against the device in order to maintain the thinnest possible profile for the device, prevent inadvertent opening of the pouch, and to provide a pleasing appearance. In some embodiments, a flexible molded element is utilized to cover the device. Features that include a flexible molded element can be found as described in US Patent Application No. 2012/0283678, incorporate herein by reference for this disclosure.

Alternatively, it is possible to incorporate a film element (15) to cover the device. The film could be a flexible, non-elastic, material that fully or partially covers the device. It would hold the pouch in its thin, folded configuration while also holding the inflatable seal in place against the stoma (see, e.g., FIG. 19).

The cover, in one embodiment, could be open at the bottom end to allow the pouch to be pulled out from under the cover when it is time to change the device. Pulling the film out from the cover, by means of a protruding tab (16) or other means of engaging the pouch, would allow the pouch to be unfolded and fill with stool as the seal is pulled away from the stoma (see FIG. 20).

Alternatively, in other embodiments, the cover could have one of more weakened areas such as lines of perforations (17). By inserting a finger under the cover and lifting, the cover could be intentionally torn to release the folded pouch (see, e.g., FIGS. 21 and 22).

In some embodiments, the cover could be attached one or more points, or continuously around its outer edge, to the wafer as an anchoring means.

In some embodiments, the devices described herein may be used as a self-contained, single-use device. That is, the sealing element, vent and filter system, containment pouch, and adhesive wafer are all integral elements of the same, single-use device. The entire device is removed by deploying the pouch, pulling the seal away from the stoma, allowing the pouch to fill with effluent, and then removing the adhesive from the peristomal area of the wearer. After removal, the device is disposed of and is replaced by an identical device or by a standard ostomy pouch.

In yet other embodiments, the devices disclosed herein could be designed to removably attach to a "two-piece" style of ostomy wafer by means of a coupling system (18). Removal of a two-piece version of the device would be accomplished as above, but with the final step of removing the device from the ostomy wafer and leaving the ostomy wafer in place (see, e.g., FIG. 23).

In some embodiments, the abovementioned cover, in the event that a two-piece attachment approach is employed, could be attached to the coupling. In some embodiments, for ostomates with firm stool and/or regular and predictable bowel activity, a device is produced as above, including the embodiments as described above, but without an inflatable seal. Instead, the interior volume of the device would at least partially fill with stool (19) as it is expelled from the stoma. In this design, the stool expelled from the stoma becomes trapped above the stoma and effectively functions as a temporary seal (see FIG. 24).

For a device of this type to function effectively, it is important that it maintain an effective venting path in the presence of stool. One such vent path would feature a large area flow path and would include a multiple of tortuous paths to maintain effective venting even if a large percentage of the vent path is clogged. As described above, that flow path would usually, but not always, include a filter for deodorization.

In some embodiments of this type of filter, the devices disclosed would incorporate a filter (5) attached to the outer film wall of the pouch. It would also incorporate a pre-filter (7) featuring a tortuous path to protect the filter. One such pre-filter would consist of open cell foam. It may be desirable to direct flow into the pre-filter by means of a protective baffle (20) that would limit access to it only from specific directions. For example, the baffle could be fixed in place, by means of welding, adhesives, or discrete fasteners, so that access to the pre-filter would be limited to an inwardly radial path (see FIG. 25).

In some embodiments, and in order to accommodate a full range of stoma protrusions, the devices disclosed herein may incorporate a means of accommodating a stoma with higher protrusion. Such means could include a larger cover that would extend further when the appliance is worn. Alternatively, a two-piece coupling with a taller profile would accommodate a stoma with higher protrusion.

What is claimed is:

1. An ostomy pouch comprising an adhesive collar comprising an adhesive to secure the pouch around a stoma, wherein the adhesive collar is attached to the pouch around a stomal opening for fitting around the stoma, and the adhesive in the adhesive collar is attached to an inside of the pouch, and wherein the pouch comprises a segmented release liner configured to allow manipulation of the adhesive through the pouch and a release coated sheet configured to prevent blocking of the pouch during storage or use.

2. The ostomy pouch of claim 1, wherein the adhesive collar is heart shaped as configured to increase adhered skin area by the adhesive to the adhesive collar in 3 and 9 o'clock positions of the stoma and reduce adhered skin area at a top or 12 o'clock position of the stoma.

3. The ostomy pouch of claim 2, wherein the adhesive collar is heart shaped as configured to increase adhered skin area by the adhesive to the adhesive collar at a 6 o'clock position of the stoma.

4. The ostomy pouch of claim 1, wherein the release coated sheet is between a front pouch panel and the adhesive collar, said release coated sheet comprises a flexible film or paper.

5. The ostomy pouch of claim 4, wherein the flexible film comprises a coating of polyethylene, polypropylene, polyester, EVA, polyamide or polycarbonate.

6. The ostomy pouch of claim 1, further comprising a stoma viewing mechanism including a partially or totally opaque sheet of material, said partially or totally opaque sheet of material comprises a flap, wherein the flap:
   a. attaches at a flap peripheral edge to a panel peripheral edge of a front panel of the pouch,
   b. has a covering pouch portion covering a covered portion of the front panel of the pouch that has more than about 50% of its perimeter of the flap peripheral edge detached from the front panel of the pouch, and
   c. is configured to tuck or fold into the ostomy pouch to maintain a stoma viewing position without continuously contacted by an opening force or mechanism.

7. The ostomy pouch of claim 6, wherein the flap attached at the flap peripheral edge to the panel peripheral edge of the front panel of the pouch has more than about 65% of its perimeter detached from the front panel of the pouch.

8. The ostomy pouch of claim 6, wherein the flap attached at the flap peripheral edge to the panel peripheral edge of the front panel of the pouch has more than about 80% of its perimeter detached from the front panel of the pouch.

9. The ostomy pouch of claim 6, wherein the flap reveals more than 60% of the covered portion of the front panel of the pouch when manually manipulated to the stoma viewing position by 2 or fewer digits of a hand.

10. The ostomy pouch of claim 6, wherein the flap reveals more than 70% of the covered portion of the front panel of the pouch when manually manipulated to the stoma viewing position by 2 or fewer digits of a hand.

11. The ostomy pouch of claim 6, wherein the flap reveals more than 75% of the covered portion of the front panel of the pouch when manually manipulated to the stoma viewing position by 2 or fewer digits of a hand.

12. The ostomy pouch of claim 6, wherein the stoma viewing mechanism can conceal and or hide the stoma and the pouch contents as needed.

13. The ostomy pouch of claim 6, wherein the flap is held closed by adhering to the front panel of the pouch via a pressure sensitive adhesive, hook and loop, or a sleeve mechanism.

14. The ostomy pouch of claim 6, wherein the flap is held closed by the pouch film or comfort panel extended from the covered portion of the front panel of the pouch by either a hook or a loop portion of a hook and loop or a hook and hook fastening system, and the pouch film or comfort panel comprising a corresponding and opposing hook or loop of the fastening system.

* * * * *